United States Patent [19]

Grollier et al.

[11] Patent Number: 4,840,790
[45] Date of Patent: * Jun. 20, 1989

[54] COSMETIC COMPOSITION FOR THE TREATMENT OF THE HAIR AND SCALP CONTAINING IN COMBINATION A POLY-BETA-ALANINE AND NICOTINIC ACID OR AN ESTER THEREOF

[75] Inventors: Jean-Francois Grollier; Chantal Fourcadier, both of Paris, France

[73] Assignee: L'Oreal, Paris, France

[*] Notice: The portion of the term of this patent subsequent to Apr. 5, 2005 has been disclaimed.

[21] Appl. No.: 865,441

[22] Filed: May 21, 1986

[30] Foreign Application Priority Data

May 22, 1985 [FR] France .................................. 85 07703

[51] Int. Cl.⁴ .............................................. A61K 7/06
[52] U.S. Cl. ....................................................... 424/70
[58] Field of Search .............................. 424/70; 524/99

[56] References Cited

U.S. PATENT DOCUMENTS 4,735,797  4/1988  Grollier et al. ...................... 424/47

FOREIGN PATENT DOCUMENTS 109353  4/1981  Japan ...................................... 424/70

OTHER PUBLICATIONS

J. S. Strauss & E. Pochi, "The Hormonal Control of The Pilosebaceous Unit", p. 240 *Biology and Disease of the Hair*, ed. Kobori & Montagna, 1976.

*Primary Examiner*—Joseph L. Schofer
*Assistant Examiner*—Jeffrey T. Smith
*Attorney, Agent, or Firm*—Cushman, Darby & Cushman

[57] ABSTRACT

A cosmetic composition for the treatment of the hair and scalp comprises in a cosmetically acceptable vehicle a combination of a water soluble polyamide of the poly-beta-alanine type and a nicotinic derivative selected from nicotinic acid or an ester thereof. This composition is employed in a process for improving the regrowth of hair and for delaying or retarding the appearance of an oily aspect of the hair.

12 Claims, No Drawings

COSMETIC COMPOSITION FOR THE TREATMENT OF THE HAIR AND SCALP CONTAINING IN COMBINATION A POLY-BETA-ALANINE AND NICOTINIC ACID OR AN ESTER THEREOF

The present invention relates to a cosmetic composition for the treatment of the hair and scalp comprising, in combination, a water soluble polyamide of the poly-beta-alanine type and nicotinic acid or an ester thereof.

To improve the regrowth of hair, there are employed certain capillary compositions which are often termed "anti-fallout" compositions. Known hair regrowth compositions contain nicotinic acid or an ester thereof, because of their rubefacient and vasodilator activity when applied to the scalp.

It is also known to combine esters of nicotinic acid with conventional cosmetic resins so as to provide capillary lotions, lacquers and hair setting lotions.

However, the use of such capillary compositions for improving hair regrowth entails, more often than not, the disadvantage of imparting to the hair an unesthetic appearance.

In particular, the use of known anti-fallout compositions does not prevent the appearance of an oily aspect of the hair and sometimes it even aggravates this phenomenon.

It is also known that hair fallout is often associated with the production of excessive sebum, these two phenomena being simultaneously stimulated by an endocrinologic mechanism under the influence of androgenes; see principally the article by John S. Strauss and Peter E. Pochi, entitled: "The Hormonal Control of the Philosebaceous Unit", p. 240, in the publication "Biology and Disease of the Hair", Ed. Kobori and Montagna (1976).

Consequently, a thinness in the appearance of hair which is a characteristic of the hair of persons experiencing a hair fallout phenomenon is further accentuated by an excessive production of sebum which causes the hair to stick together and causes any hairstyle to lie flat on the head.

This appearance of an oily aspect of the hair which is observed in a significant percent of individuals is due to the secretion of sebum by the sebaceous glands and this phenomenon is known as hair "re-oiling". In other words, it is often said that such individuals have "oily" hair.

Consequently, there exists in the cosmetic industry a need for a composition which will not only be effective against hair fallout, but also will suppress or diminish a thinness of hair which is associated with this hair reoiling phenomenon.

In particular, before regrowth of new hair is sufficient to give visible results, which often requires several months, it has been considered advantageous to be able to provide a capillary lotion which would impart an appearance of an abundance of hair during an anti-fallout treatment.

In Belgian Pat. No. 893,738, there is described the use of water soluble polyamindes of the poly-beta-alanine type in cosmetic compositions for the hair. These compositions impart to the hair good hold and volume, so as to obtain full hair styles.

The applicants have now discovered, in a surprising fashion, and contrary to the previously described formulations, that the combination of certain water soluble polyamides of the poly-beta-alanine type with nicotinic acid or an ester thereof, provides an appearance of having an abundance of hair, as well as facilitates the creation of bouffant hair styles for alopecic subjects, during the course of a treatment to improve hair regrowth.

The present invention thus relates to new cosmetic compositions for the treatment of the hair and scalp, characterized essentially by the fact that they contain, in combination, on the one hand at least one water soluble polyamide of the poly-beta-alanine type and on the other hand at least one nicotinic derivative selected from nicotinic acid or an ester thereof.

These new compositions have then for an effect not only an improvement in hair regrowth, but they also retard the appearance of an oily aspect of hair, thereby improving the holding characteristics of full or bouffant hair styles.

It is appropriate to note that the compositions of the present invention do not appear to act on the production of sebum, but rather on the aspect of the hair, that is to say, truly, on the distribution of the sebum on the hair.

The cosmetic compositions of the present invention can also include known active components, and in particular other anti-fallout agents such as vitamin F or amniotic liquid.

The water soluble polyamide of the poly-beta-alanine type, employed in the capillary cosmetic composition of the present invention, is principally a water soluble polyamide containing from 50 to 100 percent of units of Formula I:

$$\pm CH_2-CH_2-CO-NH\pm \qquad (I)$$

and from 0 to 50 percent of units of Formula II:

$$\pm CH_2-CH\pm \atop | \atop CONH_2 \qquad (II)$$

Such water soluble polyamides of the poly-beta-alanine type (called hereafter "poly-beta-alanines") are described in U.S. Pat. No. 4,082,730 and in Belgian Pat. No. 893,738, or they can be obtained in accordance with methods analogous to those described in these patents.

The water soluble poly-beta-alanines useful in the compositions of the present invention generally have a molecular weight ranging from 500 to 200,000, preferably from 2,000 to 100,000 and more preferably from 50,000 to 100,000, the molecular weight being determined in accordance with light diffusion methods.

In the compositions of the present invention, the amount of the poly-beta-alanine can vary generally from 0.1 to 5 weight percent and in particular from 0.3 to 2 weight percent based on the total weight of the composition.

The nicotinic acid or ester thereof is present, in the compositions of the present invention, in an amount ranging from 0.05 to 5 weight percent, and in particular, from 0.05 to 1 weight percent, based on the total weight of the composition.

The ester of nicotinic acid employed in the compositions of the present invention is preferably a $C_1$–$C_6$ alkyl ester, in particular the methyl ester, or the benzyl ester.

When the composition of the present invention contains vitamin F, it is present generally in an amount of 0.01 to 5 weight percent, and in particular from 0.05 to 2 weight percent based on the total weight of the composition.

A preferred composition, according to the present invention, is one which contains 0.5 to 2 weight percent of poly-beta-alanine, 0.1 to 1 weight percent of nicotinic acid or an ester thereof and 0.1 to 2 weight percent of vitamin F.

The vehicle or carrier employed in the compositions of the present invention can be a known liquid cosmetically acceptable vehicle capable of dissolving the active components employed. Preferably an aqueous vehicle comprising water or a hydroalcoholic mixture is employed, the alcohol moiety in the latter being, preferably, an alkanol having 1-4 carbon atoms, and in particular, ethanol or isopropyl alcohol.

The compositions of the invention can also contain at least one conventional adjuvant such as perfumes, coloring agents, preservatives, pH modifiers, softening agents, sequesterants, foam stabilizers, UV absorbers, peptizing agents, surfactants, antioxidants, thickening agents and the like, so as to provide the compositions under the appropriate form and to permit their use and their preservation.

The pH of the compositions of the present invention can vary from 3 to 10.

These compositions are provided principally in the form of non-rinse products such as lotions, styling foams, hair setting lotions, hair shaping lotions, brushing lotions or gels, which are prepared in accordance with conventional procedures.

These compositions can also be provided in the form of pressurized compositions for aerosols, sprays or foams, in combination with a propellant. As the propellant there can be employed $CO_2$, nitrogen, nitrogen oxide or volatile hydrocarbons such as butane, isobutane, propane or, preferably chlorinated and/or fluorinated hydrocarbons.

The present invention also relates to new industrially packaged cosmetic compositions, comprising a composition such as defined above, in combination with an appropriate packaging means and with directions for use containing written instructions for using the composition, so as to improve hair regrowth and to retard or delay the appearance of an oily aspect of the hair.

The present invention also relates to the use of, as an active component in the preparation of cosmetic compositions intended to improve the hair regrowth and to delay or retard the appearance of an oily aspect of the hair, at least one water soluble polyamide of the poly-beta-alanine type in combination with nicotinic acid or an ester thereof.

The present invention further relates to a process for treating hair comprising, principally, applying to the hair and scalp of a person, principally an alopecic person, a composition such as defined above, in an amount sufficient to impregnate the hair and scalp.

After the hair has been impregnated with the composition of the present invention, the hair can be dried. However, it is also possible to set the hair in any desired configuration or style before drying it.

The following non-limiting examples are given to illustrate the invention.

EXAMPLE 1

A capillary lotion is prepared by admixing the following components:

| | |
|---|---|
| Methyl nicotinate | 0.5 g (A.M.-active material) |
| Poly-beta-alanine, M.W. = 80,000 | 0.5 g (A.M.) |
| Ethyl alcohol, 96% vol. | 42.5 g |
| Perfume, coloring agent, preservative, sufficient amount | |
| 2-amino-2-methyl-1-propanol sufficient amount for pH = 7 | |
| Water, sufficient amount for | 100 g |

EXAMPLE 2

A capillary fluid gel is prepared having the following composition:

| | |
|---|---|
| Methyl nicotinate | 0.3 g (A.M.) |
| Poly-beta-alanine, M.W. = 80,000 | 0.5 g (A.M.) |
| Vitamin F | 1 g (A.M.) |
| Xanthane gum, sold by Rhone Poulenc under the trade name "Rhodopol 23 U" | 0.5 g |
| Ethyl alcohol, 96% vol. | 42.5 g |
| Perfume, coloring agent, preservative, sufficient amount | |
| 2-amino-2-methyl-1-propanol, sufficient amount for pH = 7 | |
| Water, sufficient amount for | 100 g |

EXAMPLE 3

A foam packaged in an aerosol container is prepared having the following composition:

| | |
|---|---|
| Nicotinic acid | 0.1 g (A.M.) |
| Poly-beta-alanine, M.W. = 80,000 | 0.5 g (A.M.) |
| Vitamin F | 0.1 g (A.M.) |
| Non-ionic surfactant (produced in accordance with French patent 71.17206 (2.091.516) by condensing 3.5 moles of glycidol on a $C_{11}$-$C_{14}$ α-diol) | 0.5 g |
| Perfume, coloring agent, preservative, sufficient amount | |
| 2-amino-2-methyl-1-propanol, sufficent amount for pH = 7 | |
| Water, sufficient amount for | 100 g |

The above composition is packaged in an aerosol container under pressure so that the final formulation is as follows:

| | |
|---|---|
| Composition, given above | 90 g |
| Freon 12/114 propellant, 50/50 weight mixture | 10 g |
| Total | 100 g |

EXAMPLE 4

A lotion having the following composition is prepared:

| | |
|---|---|
| Benzyl nicotinate | 0.2 g (A.M.) |
| Poly-beta-alanine, M.W. = 80,000 | 0.5 g (A.M.) |
| Ethyl alcohol, 96% vol. | 42.5 g |
| Perfume, coloring agent, preservative, sufficient amount | |
| 2-amino-2-methyl-1-propanol, sufficient amount for pH = 7 | |
| Water, sufficient amount for | 100 g |

What is claimed is:

1. A cosmetic composition for the hair to retard the appearance of an oily aspect of the hair comprising in a cosmetically acceptable vehicle
   (i) a water soluble polymer comprising 50 to 100% of units of the formula $-\!\!-\!\![CH_2-\!\!-CH_2-\!\!-CO-\!\!-NH]\!\!-\!\!-$ and from 0 to 50% of units of the formula

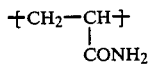

and
   (ii) at least one nicotinic derivative selected from nicotinic acid or an ester thereof.

2. The composition of claim 1 wherein the ester of nicotinic acid is a $C_1$-$C_6$ alkyl ester or a benzyl ester thereof.

3. The composition of claim 3 wherein the ester of nicotinic acid is methyl nicotinate.

4. The composition of claim 1 wherein said water soluble polymer is present in an amount ranging from 0.1 to 5 weight percent based on the total weight of said composition.

5. The composition of claim 1 wherein said water soluble polymer is present in an amount ranging from 0.3 to 2 weight percent based on the total weight of said composition.

6. The composition of claim 1 wherein said nicotinic derivative is present in an amount ranging from 0.05 to 5 weight percent based on the total weight of said composition.

7. The composition of claim 1 wherein said nicotinic derivative is present in an amount ranging from 0.05 to 1 weight percent based on the total weight of said composition.

8. The composition of claim 1 comprising, based on the total weight thereof, 0.5 to 2 weight percent of said water soluble polymer, and 0.1-1 weight percent of said nicotinic derivative, said composition also containin 0.1-2 weight percent of vitamin F.

9. The composition of claim 1 in the form of a non-rinse lotion, styling foam, hair shaping lotion, hair setting lotion, brushing lotion or gel.

10. The composition of claim 1 in the form of a pressurized composition for an aerosol, spray or foam, in combination with a propellant.

11. A process for the cosmetic treatment of the hair so as to improve hair regrowth and to delay or retard the appearance of an oily aspect of said hair comprising applying to the hair and scalp the cosmetic composition of claim 1 in an amount sufficient to impregnate the hair and scalp.

12. A cosmetic composition for the treatment of the hair and scalp so as to improve hair regrowth and delay the appearance of an oily aspect of the hair, said composition comprising in an aqueous or hydroalcoholic vehicle
   (1) a water soluble polymer containing from 50 to 100% of units of the formula $-\!\!-\!\![CH_2-\!\!-CH_2-\!\!-CO-\!\!-NH]\!\!-\!\!-$ and from 0 to 50% of units having the formula

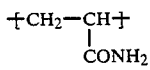

and having a molecular weight ranging from 500 to 200,000, said water soluble polymer being present in an amount ranging from 0.1 to 5 weight percent based on the total weight of said compositions, and
   (2) a nicotinic derivative selected from the group consisting of nicotinic acid, a $C_1$-$C_6$ alkyl ester of nicotinic acid and the benzyl ester of nicotinic acid, said nicotinic derivative being present in an amount ranging from 0.05 to 5 weight percent based on the total weight of said composition.

* * * * *